(12) United States Patent
Sowards et al.

(10) Patent No.: US 12,232,818 B2
(45) Date of Patent: Feb. 25, 2025

(54) SYSTEM AND METHOD FOR OPTIC SHAPE SENSING AND ELECTRICAL SIGNAL CONDUCTION

(71) Applicant: Bard Access Systems, Inc., Salt Lake City, UT (US)

(72) Inventors: Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 962 days.

(21) Appl. No.: 17/191,551

(22) Filed: Mar. 3, 2021

(65) Prior Publication Data

US 2021/0275256 A1    Sep. 9, 2021

Related U.S. Application Data

(60) Provisional application No. 62/984,552, filed on Mar. 3, 2020.

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/065* (2013.01); *A61B 5/318* (2021.01);
(Continued)

(58) Field of Classification Search
None
See application file for complete search history.

(56) References Cited

U.S. PATENT DOCUMENTS

| 3,493,288 A | 2/1970 | Oltman et al. |
| 4,768,855 A | 9/1988 | Nishi et al. |

(Continued)

FOREIGN PATENT DOCUMENTS

| CA | 3025240 A1 | 11/2017 |
| DE | 102016109601 A1 | 11/2017 |

(Continued)

OTHER PUBLICATIONS

PCT/US2021/024969 filed Mar. 30, 2021 International Search Report and Written Opinion dated Jul. 19, 2021.

(Continued)

*Primary Examiner* — Jerry Rahll
(74) *Attorney, Agent, or Firm* — Rutan & Tucker LLP

(57) ABSTRACT

A medical device operating as a stylet is described. The medical device can include an insulating layer (or sheath) encapsulating both a multi-core optical fiber and a conductive medium. The optical fiber can include a cladding and a plurality of core fibers spatially arranged within the cladding. Each of the core fibers can include a plurality of sensors distributed along a longitudinal length of that corresponding core fiber and each of these sensors can be configured to: (i) reflect a light signal of a different spectral width based on received incident light, and (ii) change a characteristic of the reflected light signal for use in determining a physical state of the multi-core optical fiber. The conductive medium can provide a pathway for electrical signals detected at a distal portion of the conductive medium. The conductive medium may be concentric to the cladding, but separate and adjust thereto.

33 Claims, 9 Drawing Sheets

(51) Int. Cl.
*A61B 5/318* (2021.01)
*G02B 6/02* (2006.01)
*G02B 6/12* (2006.01)
*G02B 6/42* (2006.01)

(52) U.S. Cl.
CPC ..... *G02B 6/02042* (2013.01); *G02B 6/02057*
(2013.01); *A61B 2034/2061* (2016.02); *A61B 2562/0266* (2013.01); *G02B 2006/12138* (2013.01); *G02B 6/4293* (2013.01)

(56) References Cited

U.S. PATENT DOCUMENTS

| | | | |
|---|---|---|---|
| 4,813,429 A | 3/1989 | Eshel et al. |
| 5,099,845 A | 3/1992 | Besz et al. |
| 5,163,935 A | 11/1992 | Black et al. |
| 5,178,153 A | 1/1993 | Einzig |
| 5,207,672 A | 5/1993 | Roth et al. |
| 5,211,165 A | 5/1993 | Dumoulin et al. |
| 5,220,703 A | 6/1993 | Kanayama et al. |
| 5,275,151 A | 1/1994 | Shockey et al. |
| 5,295,212 A | 3/1994 | Morton et al. |
| 5,423,321 A | 6/1995 | Fontenot |
| 5,454,807 A | 10/1995 | Lennox et al. |
| 5,517,997 A | 5/1996 | Fontenot |
| 5,599,492 A | 2/1997 | Engelson |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 5,957,831 A | 9/1999 | Adair |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,699,855 B2 | 4/2010 | Anderson et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 | 11/2015 | Ramamurthy et al. |
| 9,339,206 B2 | 5/2016 | Grunwald |
| 9,345,510 B2 | 5/2016 | Patel et al. |
| 9,360,630 B2 | 6/2016 | Jenner et al. |
| 9,549,685 B2 | 1/2017 | Cox et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 9,872,978 B1 | 1/2018 | Zaborsky et al. |
| 10,231,643 B2 | 3/2019 | Grunwald |
| 10,231,753 B2 | 3/2019 | Burnside et al. |
| 10,258,240 B1 | 4/2019 | Eberle et al. |
| 10,265,133 B1 | 4/2019 | McClellan |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,568,586 B2 | 2/2020 | Begin et al. |
| 10,603,126 B2 | 3/2020 | Karguth et al. |
| 10,620,386 B2 | 4/2020 | Van Der Mark et al. |
| 10,631,718 B2 | 4/2020 | Petroff et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,103,321 B2 | 8/2021 | Braun et al. |
| 11,123,047 B2 | 9/2021 | Jaffer et al. |
| 11,259,892 B2 | 3/2022 | Hufford et al. |
| 11,284,916 B2 | 3/2022 | Patel et al. |
| 11,382,653 B2 | 7/2022 | Patel et al. |
| 11,474,310 B2 | 10/2022 | Sowards et al. |
| 11,525,670 B2 | 12/2022 | Messerly et al. |
| 11,547,282 B2 | 1/2023 | Weise et al. |
| 11,607,150 B2 | 3/2023 | Schweikert et al. |
| 11,621,518 B2 | 4/2023 | Stats et al. |
| 11,707,205 B2 | 7/2023 | Messerly et al. |
| 11,806,096 B2 | 11/2023 | Flatt et al. |
| 11,850,073 B2 | 12/2023 | Wright et al. |
| 11,931,112 B2 * | 3/2024 | Thompson ........ A61M 25/0097 |
| 2002/0019627 A1 | 2/2002 | Maguire et al. |
| 2002/0087206 A1 | 7/2002 | Hirschberg et al. |
| 2002/0166109 A1 | 11/2002 | Miyake et al. |
| 2002/0198457 A1 | 12/2002 | Tearney et al. |
| 2003/0045798 A1 * | 3/2003 | Hular .................. A61B 5/6848 |
| | | 600/476 |
| 2003/0092995 A1 | 5/2003 | Thompson |
| 2004/0111020 A1 | 6/2004 | Long |
| 2004/0111147 A1 | 6/2004 | Rabkin et al. |
| 2004/0242995 A1 | 12/2004 | Maschke |
| 2004/0260182 A1 | 12/2004 | Zuluaga et al. |
| 2005/0033264 A1 | 2/2005 | Redinger |
| 2006/0013523 A1 | 1/2006 | Childers et al. |
| 2006/0036164 A1 | 2/2006 | Wilson et al. |
| 2006/0100610 A1 | 5/2006 | Wallace et al. |

(56) References Cited

U.S. PATENT DOCUMENTS

| | | |
|---|---|---|
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Arkin et al. |
| 2007/0179485 A1 | 8/2007 | Yeik et al. |
| 2007/0201793 A1 | 8/2007 | Askins et al. |
| 2007/0253673 A1 | 11/2007 | Nielsen et al. |
| 2007/0287886 A1 | 12/2007 | Saadat |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 | 1/2009 | Dick et al. |
| 2009/0046980 A1 | 2/2009 | Rohlen |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0304582 A1 | 12/2009 | Rousso et al. |
| 2009/0318757 A1 | 12/2009 | Singh |
| 2009/0324161 A1* | 12/2009 | Prisco ............ G01L 1/246 385/12 |
| 2010/0016729 A1 | 1/2010 | Futrell |
| 2010/0030063 A1* | 2/2010 | Lee ............ A61B 5/06 600/424 |
| 2010/0063534 A1 | 3/2010 | Kugler et al. |
| 2010/0114115 A1 | 5/2010 | Schlesinger et al. |
| 2010/0114190 A1 | 5/2010 | Bendett et al. |
| 2010/0139669 A1 | 6/2010 | Piferi et al. |
| 2010/0204569 A1 | 8/2010 | Burnside et al. |
| 2010/0286531 A1 | 11/2010 | Ryan et al. |
| 2010/0292758 A1 | 11/2010 | Lee et al. |
| 2011/0087112 A1* | 4/2011 | Leo ............ A61B 90/98 600/478 |
| 2011/0098533 A1 | 4/2011 | Onoda et al. |
| 2011/0144481 A1 | 6/2011 | Feer et al. |
| 2011/0144630 A1 | 6/2011 | Loeb |
| 2011/0166442 A1 | 7/2011 | Sarvazyan |
| 2011/0172680 A1 | 7/2011 | Younge et al. |
| 2011/0178509 A1 | 7/2011 | Zerfas et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1 | 6/2013 | Manzke et al. |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0031674 A1 | 1/2014 | Newman et al. |
| 2014/0046261 A1 | 2/2014 | Newman et al. |
| 2014/0058368 A1 | 2/2014 | Hogue |
| 2014/0088413 A1 | 3/2014 | Von Bucsh et al. |
| 2014/0121468 A1 | 5/2014 | Eichenholz |
| 2014/0188133 A1 | 7/2014 | Misener |
| 2014/0221829 A1 | 8/2014 | Maitland et al. |
| 2014/0259477 A1 | 9/2014 | Huang |
| 2014/0275997 A1 | 9/2014 | Chopra et al. |
| 2014/0318825 A1 | 10/2014 | Erb et al. |
| 2014/0378945 A1 | 12/2014 | Beri |
| 2015/0029511 A1 | 1/2015 | Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1* | 12/2016 | Swanson ............ G01B 9/02028 |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1 | 10/2017 | Schlesinger et al. |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2018/0369432 A1 | 12/2018 | Zaborsky |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0223706 A1* | 7/2019 | Takeuchi ............ A61B 1/07 |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1 | 12/2019 | Courtney et al. |
| 2020/0046434 A1 | 2/2020 | Graetzel et al. |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |

(56) References Cited

U.S. PATENT DOCUMENTS

| | | |
|---|---|---|
| 2021/0030504 A1 | 2/2021 | Thompson et al. |
| 2021/0045814 A1 | 2/2021 | Thompson et al. |
| 2021/0298680 A1 | 3/2021 | Sowards et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0278604 A1 | 9/2021 | Rohr Daniel et al. |
| 2021/0282867 A1 | 9/2021 | Tegg et al. |
| 2021/0325172 A1 | 10/2021 | Hendriks et al. |
| 2021/0330398 A1* | 10/2021 | Tegg .................. A61B 34/20 |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2023/0082991 A1 | 3/2023 | Sowards et al. |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 3545849 A1 | 10/2019 |
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

U.S. Appl. No. 17/185,777, filed Feb. 25, 2021 Notice of Allowance dated Jun. 10, 2022.

PCT/US2021/038899 filed Jun. 24, 2021 International Search Report and Written Opinion dated Oct. 6, 2021.

PCT/US2021/038954 filed Jun. 24, 2021 International Search Report and Written Opinion dated Oct. 28, 2021.

PCT/US2021/041128 filed Jul. 9, 2021 International Search Report and Written Opinion dated Oct. 25, 2021.

PCT/US2021/044216 filed Aug. 2, 2021 International Search Report and Written Opinion dated Nov. 18, 2021.

U.S. Appl. No. 17/185,777, filed Feb. 25, 2021 Non-Final Office Action dated Feb. 9, 2022.

PCT/US2018/026493 filed Apr. 6, 2018 International Search Report and Written Opinion dated Jun. 22, 2018.

PCT/US2020/044801 filed Aug. 3, 2020 International Search Report and Written Opinion dated Oct. 26, 2020.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

U.S. Appl. No. 15/947,267, filed Apr. 6, 2018 Final Office Action dated Jun. 30, 2021.

U.S. Appl. No. 15/947,267, filed Apr. 6, 2018 Final Office Action dated Nov. 10, 2020.

U.S. Appl. No. 15/947,267, filed Apr. 6, 2018 Non-Final Office Action dated Mar. 12, 2021.

U.S. Appl. No. 15/947,267, filed Apr. 6, 2018 Non-Final Office Action dated May 29, 2020.

U.S. Appl. No. 15/947,267, filed Apr. 6, 2018 Non-Final Office Action dated Oct. 13, 2021.

PCT/US2021/054596 filed Oct. 12, 2021 International Search Report and Written Opinion dated Jan. 26, 2022.

PCT/US2022/043698 filed Sep. 15, 2022 International Search Report and Written Opinion dated Dec. 19, 2022.

U.S. Appl. No. 17/967,794, filed Oct. 17, 2022 Notice of Allowance dated Feb. 15, 2023.

PCT/US2021/059755 filed Nov. 17, 2021 International Search Report and Written Opinion dated Apr. 29, 2022.

PCT/US2021/054802 filed Oct. 13, 2021 International Search Report and Written Opinion dated Feb. 2, 2022.

PCT/US2021/060849 filed Nov. 24, 2021 International Search Report and Written Opinion dated Mar. 9, 2022.

U.S. Appl. No. 15/947,267, filed Apr. 6, 2018 Final Office Action dated Apr. 22, 2022.

PCT/US2022/024934 filed Apr. 14, 2022 International Search Report and Written Opinion dated Jul. 18, 2022.

PCT/US2023/020042 filed Apr. 26, 2023 International Search Report and Written Opinion dated Sep. 26, 2023.

PCT/US2023/025757 filed Jun. 20, 2023 International Search Report and Written Opinion dated Sep. 11, 2023.

PCT/US2023/027527 filed Jul. 12, 2023 International Search Report and Written Opinion dated Oct. 16, 2023.

(56) References Cited

OTHER PUBLICATIONS

U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/217,852, filed Mar. 30, 2021 Ex Parte Quayle Action dated Sep. 8, 2023.
U.S. Appl. No. 17/217,852, filed Mar. 30, 2021 Notice of Allowance dated Nov. 7, 2023.
U.S. Appl. No. 17/499,644, filed Oct. 12, 2021 Notice of Allowance dated Sep. 18, 2023.
U.S. Appl. No. 17/535,406, filed Nov. 24, 2021 Restriction Requirement dated Nov. 24, 2023.
U.S. Appl. No. 17/697,895, filed Mar. 17, 2022 Advisory Action dated Sep. 8, 2023.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Notice of Allowance dated May 8, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
PCT/US2021/020732 filed Mar. 3, 2021 International Search Report and Written Opinion dated Jul. 5, 2021.
PCT/US2020/062396 filed Nov. 25, 2020 International Search Report and Written Opinion dated Mar. 2, 2021.
PCT/US2020/062407 filed Nov. 25, 2020 International Search Report and Written Opinion dated Mar. 11, 2021.
U.S. Appl. No. 17/187,536, filed Feb. 26, 2021 Non-Final Office Action dated Dec. 15, 2023.
U.S. Appl. No. 17/535,406, filed Nov. 24, 2021 Non-Final Office Action dated Feb. 15, 2024.
U.S. Appl. No. 17/697,895, filed Mar. 17, 2022 Non-Final Office Action dated Jan. 11, 2024.
PCT/US2023/014849 filed Mar. 8, 2023 International Search Report and Written Opinion dated Jun. 7, 2023.
PCT/US2023/015416 filed Mar. 16, 2023 International Search Report and Written Opinion dated May 26, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/187,536, filed Feb. 26, 2021 Non-Final Office Action dated May 17, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.
U.S. Appl. No. 17/697,895, filed Mar. 17, 2022 Final Office Action dated Aug. 16, 2023.
U.S. Appl. No. 17/697,895, filed Mar. 17, 2022 Non Final Office Action dated Jun. 14, 2023.
PCT/US2023/015536 filed Mar. 17, 2023 International Preliminary Report on Patentability dated Sep. 10, 2024.
U.S. Appl. No. 17/187,536, filed Feb. 26, 2021 Advisory Action dated Oct. 9, 2024.
U.S. Appl. No. 17/187,536, filed Feb. 26, 2021 Final Office Action dated Jul. 2, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Final Office Action dated Aug. 1, 2024.
U.S. Appl. No. 17/535,406, filed Nov. 24, 2021 Notice of Allowance dated Oct. 23, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/725,394, filed Apr. 20, 2022 Non-Final Office Action dated Jun. 17, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Advisory Action dated Oct. 24, 2024.
U.S. Appl. No. 17/849,447, filed Jun. 24, 2022 Final Office Action dated Aug. 8, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Non-Final Office Action dated Jun. 18, 2024.
U.S. Appl. No. 18/524,620, filed Nov. 30, 2023 Notice of Allowance dated Sep. 12, 2024.

* cited by examiner

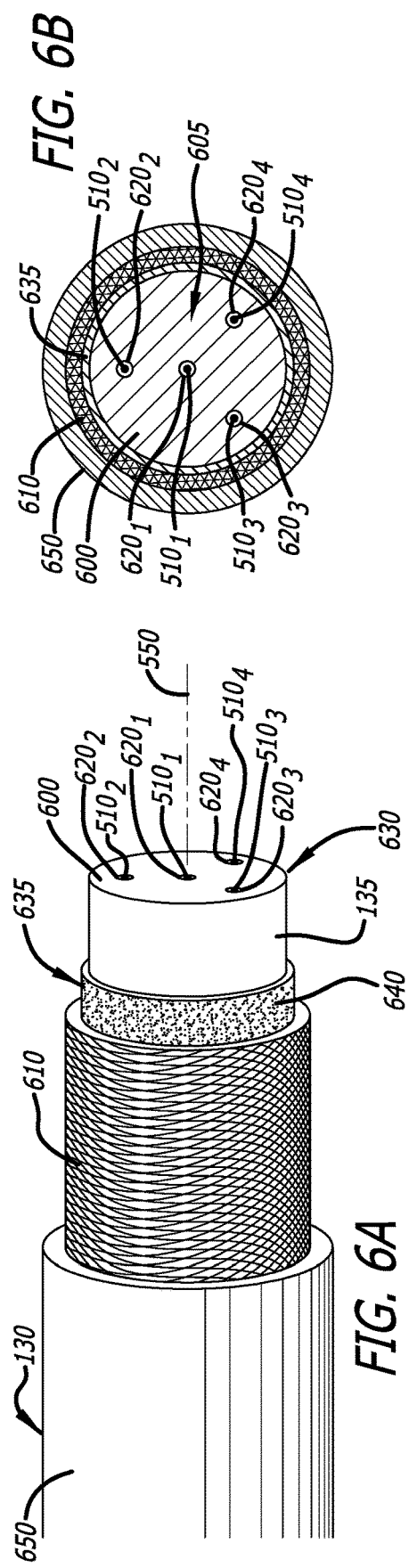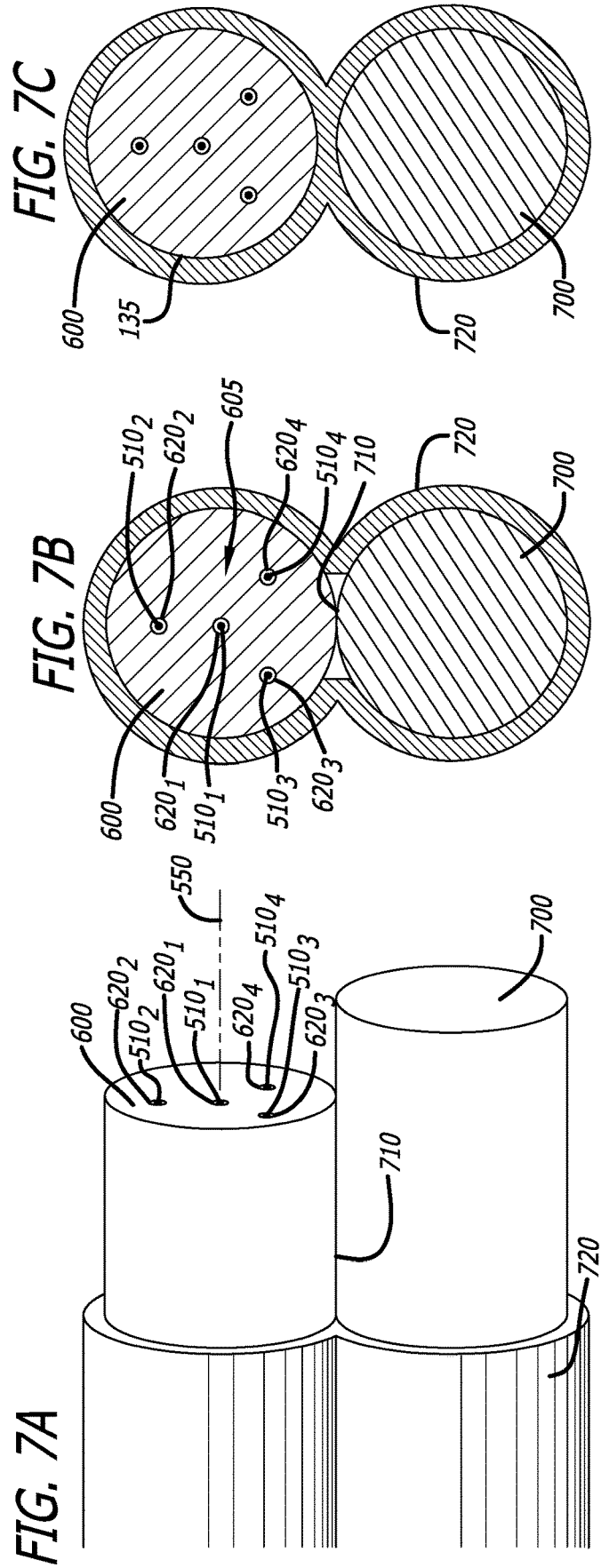

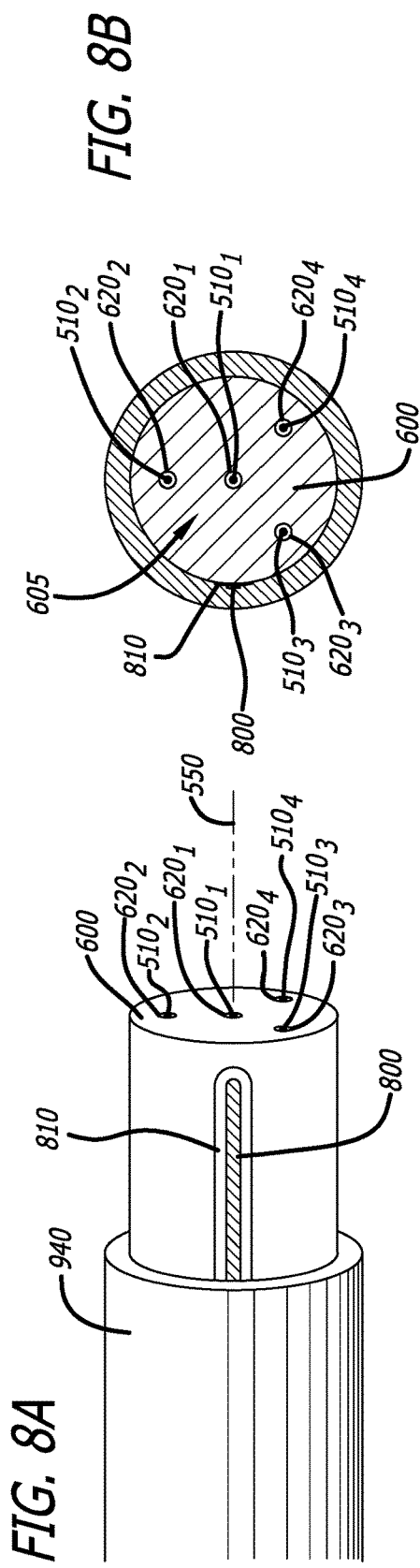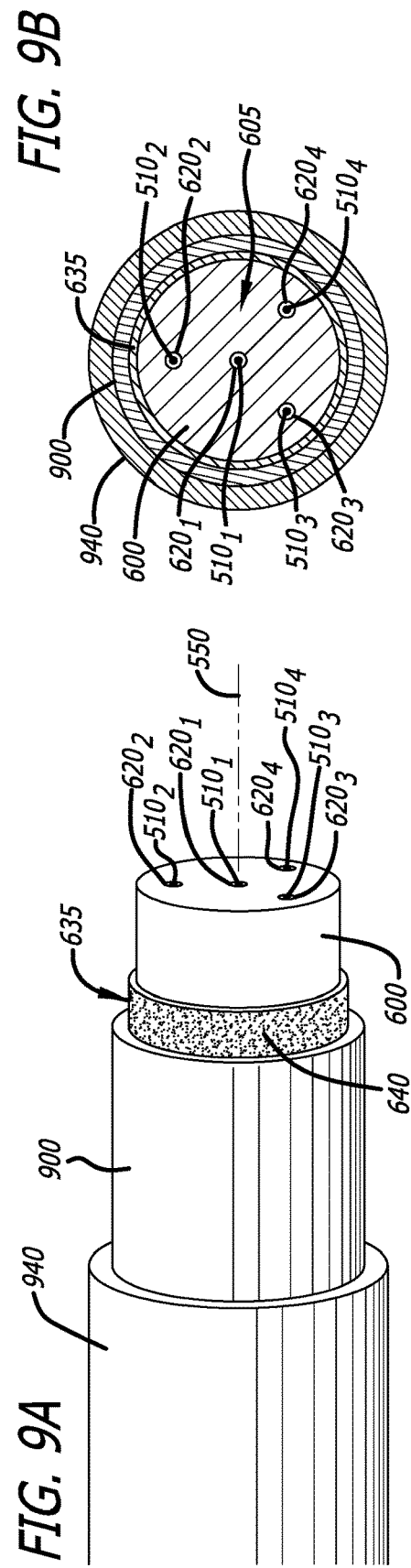

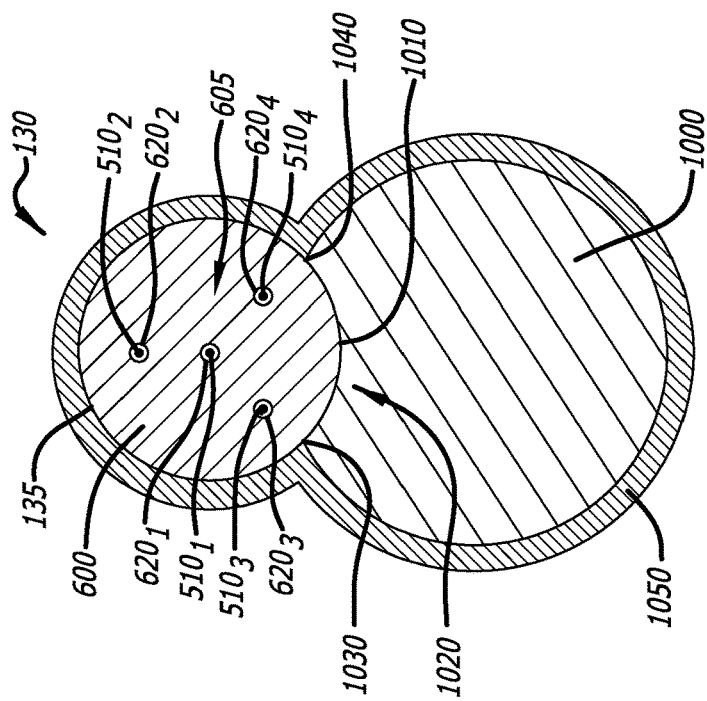
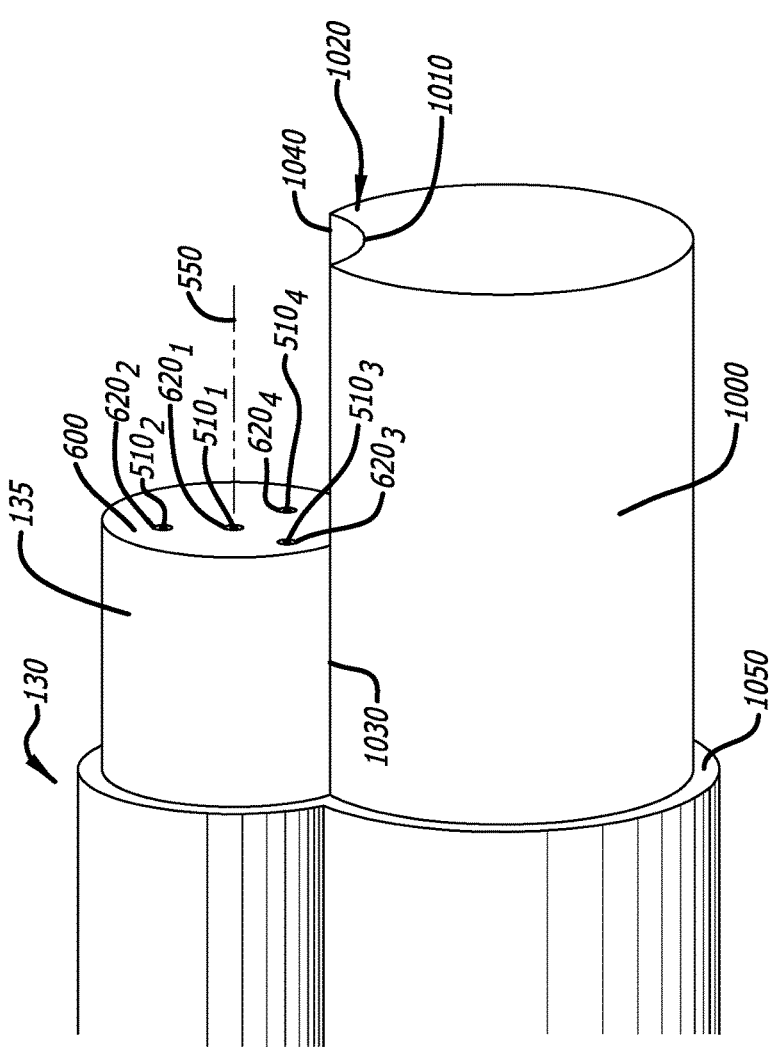

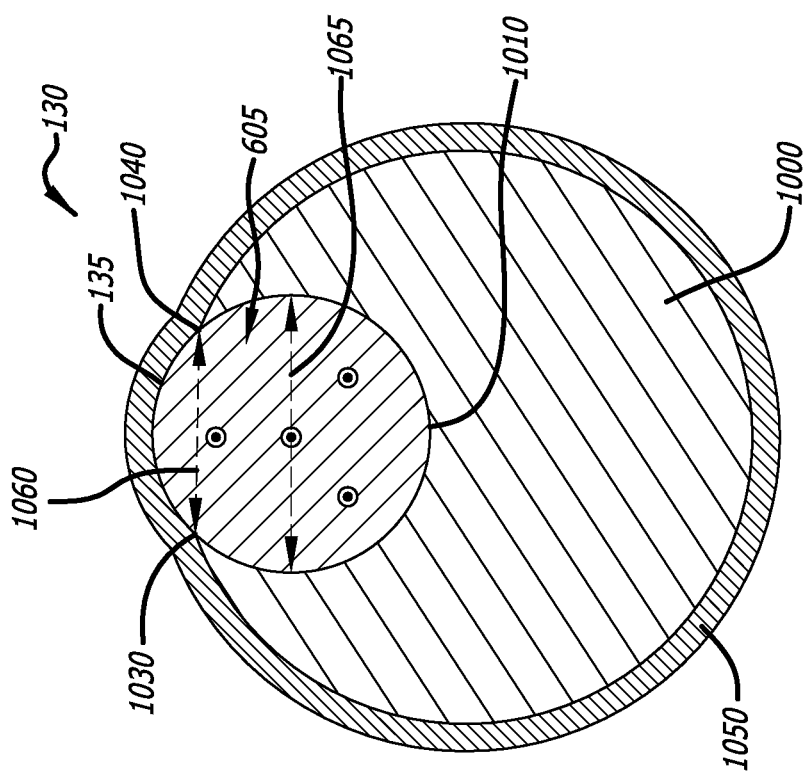
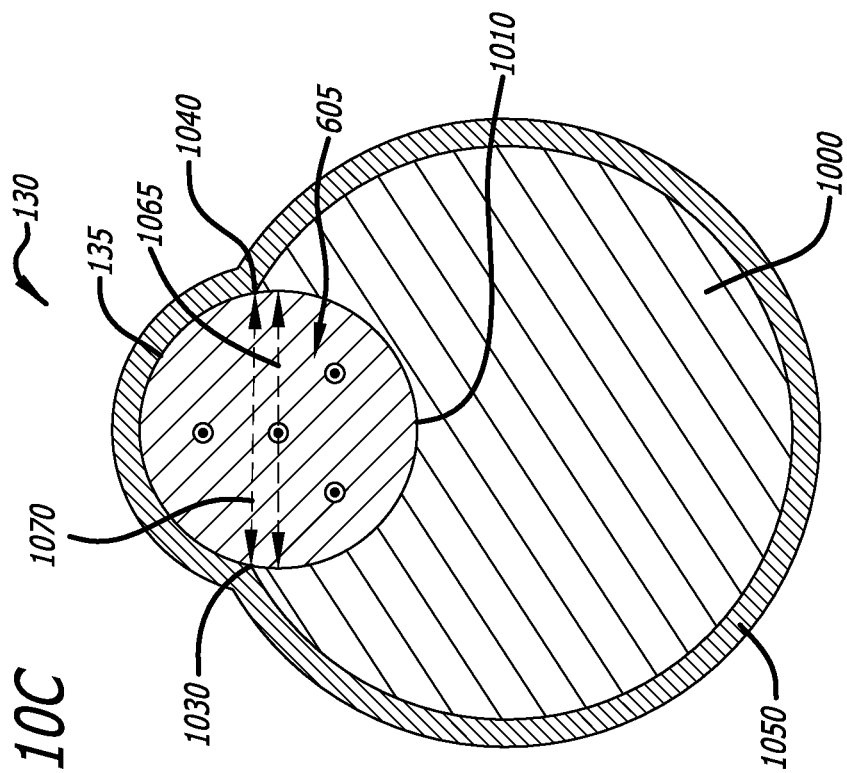

SYSTEM AND METHOD FOR OPTIC SHAPE SENSING AND ELECTRICAL SIGNAL CONDUCTION

PRIORITY

This application claims the benefit of priority to U.S. Provisional Application No. 62/984,552, filed Mar. 3, 2020, which is incorporated by reference in its entirety into this application.

BACKGROUND

In the past, certain intravascular guidance of medical devices, such as guidewires and catheters for example, have used fluoroscopic methods for tracking tips of the medical devices and determining whether the tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving multimodal stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical device may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

Disclosed herein is a fiber optic shape sensing system and methods thereof, which is not subject to the disadvantages associated with electromagnetic tracking systems as described above and is capable in its current form of providing confirmation of tip placement or information passed/interpreted as an electrical signal.

SUMMARY

Briefly summarized, embodiments disclosed herein are directed to a multimodal stylet featuring a multi-core optical fiber and a conductive medium that collectively operate for tracking placement of a catheter or other medical device within a body of a patient. Operating as a medical device, the stylet is configured to return information for use in identifying its physical state (e.g., shape length, shape, form, and/or orientation) of (i) a portion of the stylet (e.g., tip, segment of stylet, etc.) or a portion of a catheter inclusive of at least a portion of the stylet (e.g., tip, segment of catheter, etc.) or (ii) the entire or substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the multi-core optical fiber (hereinafter, "core fiber") that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber.

In some embodiments, the stylet includes a multi-core optical fiber, where each core fiber utilizes a plurality of sensors and each sensor is configured to reflect a different spectral range of the incident light (e.g., different light frequency range). Based on the type and degree of strain asserted on the each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. Herein, the shape sensing functionality is paired with the ability to simultaneously pass an electrical signal through the same member (stylet) through conductive medium included as part of the stylet.

More specifically, in some embodiments each core fiber of the multi-core optical fiber is configured with an array of sensors, which are spatially distributed over a prescribed length of the core fiber to generally sense external strain those regions of the core fiber occupied by the sensor. Given that each sensor positioned along the same core fiber is configured to reflect light of a different, specific spectral width, the array of sensors enable distributed measurements throughout the prescribed length of the multi-core optical fiber. These distributed measurements may include wavelength shifts having a correlation with strain experienced by the sensor.

According to one embodiment of the disclosure, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the stylet. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient. Herein, the core fibers are spatially separated with the cladding of the multi-mode optical fiber and each core fiber is configured to separately return light of different spectral widths (e.g., specific light wavelength or a range of light wavelengths) reflected from the distributed array of sensors fabricated in each of the core fibers. A comparison of detected shifts in wavelength of the reflected light returned by a center core fiber (operating as a reference) and the surrounding, periphery core fibers may be used to determine the physical state of the stylet.

More specifically, during vasculature insertion, the clinician may rely on the console to visualize a current physical state (e.g., shape, orientation, etc.) of a catheter guided by the stylet to avoid potential path deviations that would be caused by changes in catheter orientation. As the periphery core fibers reside at spatially different locations within the cladding of the multi-mode optical fiber, changes in orientation (e.g., angular orientation such as bending, etc.) of the stylet imposes different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (and catheter).

As an illustrative example, in the area of vascular access, the multimodal stylet would allow for additional information communicated via electrical signal (e.g., an electrocardiogram "ECG") to be passed via the conductive medium along with shape sensing information via the optical fiber from the stylet. In the case of central access, this would allow for the use of ECG confirmation techniques to be paired with a robust interpretation of the shape and position of the stylet (as well as optical fiber and/or conductive medium). As described in detail below, the multimodal stylet with the multi-core optical fiber and conductive medium may be constructed in accordance with any of a number of configurations, such as a braided configuration, parallel configuration, flex circuit configuration, conductive tubing configuration, or any other configuration selected by taking into account desired stylet rigidity and properties.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 6A is a first exemplary embodiment of the multimodal stylet of FIG. 1 supporting both an optical and electrical signaling;

FIG. 6B is a cross sectional view of the multimodal stylet of FIG. 6A;

FIG. 7A a second exemplary embodiment of the multimodal stylet of FIG. 1;

FIG. 7B is a first cross sectional view of the multimodal stylet of FIG. 7A;

FIG. 7C is a second cross sectional view of the multimodal stylet of FIG. 7A;

FIG. 8A is a third exemplary embodiment of the multimodal stylet of FIG. 1;

FIG. 8B is a cross sectional view of the multimodal stylet of FIG. 8A;

FIG. 9A is a fourth exemplary embodiment of the multimodal stylet of FIG. 1;

FIG. 9B is a cross sectional view of the multimodal stylet of FIG. 9A;

FIG. 10A a fifth exemplary embodiment of the multimodal stylet of FIG. 1;

FIG. 10B is a cross sectional view of a first embodiment of the multimodal stylet of FIG. 10A with the conductive medium partially encapsulating a portion of the optical fiber;

FIG. 10C is a cross sectional view of a second embodiment of the multimodal stylet of FIG. 10B with the conductive medium partially encapsulating a greater portion of the optical fiber;

FIG. 10D is a cross sectional view of a third embodiment of the multimodal stylet of FIG. 10A with the conductive medium encapsulating a substantial portion of the optical fiber;

DETAILED DESCRIPTION

Figure 1:
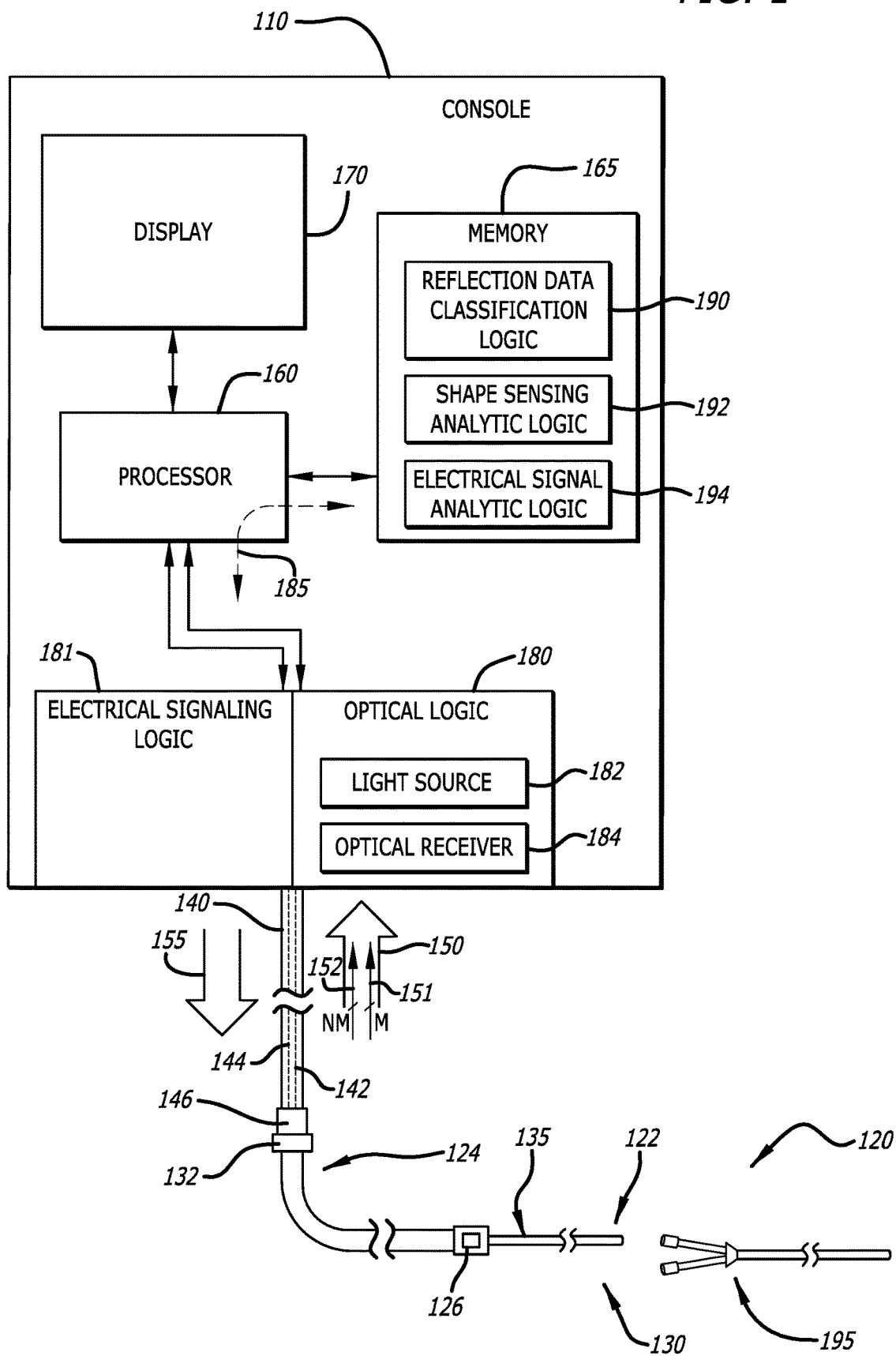
FIG. 1 is an illustrative embodiment of a medical device monitoring system.

Reference will now be made to figures wherein like structures will be provided with like reference designations. It is understood that the drawings are diagrammatic and schematic representations of exemplary embodiments of the invention, and are neither limiting nor necessarily drawn to scale.

Regarding terms used herein, it should be understood the terms are for the purpose of describing some particular embodiments, and the terms do not limit the scope of the concepts provided herein. Ordinal numbers (e.g., first, second, third, etc.) are generally used to distinguish or identify different components or operations, and do not supply a serial or numerical limitation. For example, "first," "second," and "third" components or operations need not necessarily appear in that order, and the particular embodiments including such components or operations need not necessarily be limited to the three components or operations. Similarly, labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

In the following description, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The term "logic" is representative of hardware and/or software that is configured to perform one or more functions. As hardware, logic may include circuitry having data processing and/or storage functionality. Examples of such circuitry may include, but are not limited or restricted to a processor, a programmable gate array, a microcontroller, an application specific integrated circuit, combinatorial circuitry, or the like. Alternatively, or in combination with the hardware circuitry described above, the logic may be software in the form of one or more software modules, which may be configured to operate as its counterpart circuitry. The software modules may include, for example, an executable application, a daemon application, an application programming interface (API), a subroutine, a function, a procedure, a routine, source code, or even one or more instructions. The software module(s) may be stored in any type of a suitable non-transitory storage medium, such as a programmable circuit, a semiconductor memory, non-persistent storage such as volatile memory (e.g., any type of random access memory "RAM"), persistent storage such as non-volatile memory (e.g., read-only memory "ROM", power-backed RAM, flash memory, phase-change memory, etc.), a solid-state drive, hard disk drive, an optical disc drive, or a portable memory device.

For clarity, it is to be understood that the word "proximal" refers to a direction relatively closer to a clinician using the device to be described herein, while the word "distal" refers to a direction relatively further from the clinician. Herein, the "proximal portion" of a stylet disclosed herein, for example, includes a portion of the stylet intended to be near a clinician when the stylet is used on the patient. Likewise, a "proximal end" of the stylet, for example, includes an end intended to be near the clinician when the stylet is in use. The proximal portion of the stylet may include the proximal end of the stylet; however, proximal portion of the stylet does not need to include the proximal end of the stylet.

Similarly, a "distal portion" of the stylet includes a portion of the stylet intended to be near or in a patient when the stylet is used on the patient. Likewise, a "distal end" of the stylet includes an end of the stylet intended to be near or in the patient when the stylet is in use. The distal portion of the stylet can include the distal end of the stylet; however, the distal portion of the stylet does not need include the distal end of the stylet. Also, the words "including," "has," and "having," as used herein, including the claims, shall have the same meaning as the word "comprising."

Embodiments of the disclosure are generally directed to a multimodal stylet that assists in the placement of a medical device inserted into a body of a patient. An example of such a medical device is a catheter assembly that is inserted into a vein or other vessel of the patient to infuse or aspirate fluids through one or more lumens defined by the catheter for the patient. The system utilizes multi-core optical fiber with reflective gratings in one embodiment to ascertain information regarding the optical fiber during and/or after insertion into the patient's body for rendering a shape and orientation of the stylet.

Unless defined otherwise, all technical and scientific terms used herein have the same meaning as commonly understood by those of ordinary skill in the art.

In one embodiment, the reflective gratings may include fiber Bragg gratings ("FBG") distributed along a core fiber disposed in/on the stylet (or another probe-like). An outgoing optical signal produced by a light source is incident on each of the FBGs along the core fiber, where each grating reflects light of a prescribed spectral width to produce a return optical signal to the console. According to one embodiment of the disclosure, shifts in wavelength of reflected light signals returned by each of the core fibers may be aggregated based on FBGs associated with the same cross-sectional region of the stylet (or specific spectral width) and a processor of the console may execute shape sensing analytic logic to perform analytics associated with the wavelength shifts (e.g., analysis of degree, comparison between wavelength shifts between periphery core fibers and the center core fiber or between periphery core fibers, etc.) to identify the physical state of the stylet. The data is communicated to a user of the console to identify (and render) its position within the body, two-dimensional (2-D) and three-dimensional (3-D) shape of the stylet along its length, form and shape (e.g., bending, torsion) as well as orientation (including malposition or medical device kinking), etc. Such information is presented by the console to the user in real-time to assist in guiding and placing the medical device (e.g., catheter) along with the stylet as desired within the patient. Additionally, measurements may be made by the console (e.g., ECG signaling through the conductive medium co-existing with the multi-core optical fiber) to ensure proper deployment within the patient. Further details regarding these and other embodiments are given hereafter.

Note that, though the below discussion focuses on usage of the stylet for the placement of a catheter into the body of the patient, the stylet described herein can be employed to place a variety of medical devices, especially other elongate medical devices, in a variety of locations within the patient body. As such, the principles of the present disclosure should not be considered limiting to what is explicitly described herein. Examples of catheter assemblies and medical devices that may benefit from the disclosure may include a peripherally inserted central catheter ("PICC"), central venous catheter ("CVC"), urinary catheter, midline catheter, peripheral catheter, or the like.

In light of the above, the multi-core optical fiber paired with a conductive medium for electrical signal monitoring thus serves multiple modalities. The first modality constitutes an optical modality with shape sensing functionality to determine the physical state of the stylet. The physical state of the stylet provides information to assist a clinician in guiding a catheter assembly to a desired location within the vasculature. The second modality constitutes tip location/navigation system ("TLS") modality, where the stylet with conductive medium is advanced to detect and avoid any tip malposition during such advancement. Lastly, a third modality constitutes an ECG modality, wherein ECG signal-based catheter tip guidance is employed to enable tracking and guidance of the stylet/catheter tip to a desired position with respect to a node of the patient's heart from which the ECG signals originate.

As an alternative embodiment, the conductive medium may be configured with a channel or groove in which the multi-core optical fiber may reside or one or more core fibers, separate from the multi-core optical fiber, may reside. Also, in lieu of the conductive medium positioned at the distal end of the stylet, it is contemplated that the conductive medium may extend from the console and terminate just distally from the stylet handle, coming into contact with a saline fluid path, while the multi-core optical fiber extends the length of the catheter. Hence, another conductive media (e.g., saline or another conductive fluid through a Luer connectors 340) may provide an electrically conductive path.

Referring to FIG. 1, an illustrative embodiment of a medical device monitoring system 100 is shown. As shown, the system 100 generally includes a console 110 and a handheld medical device 120 (hereinafter, "stylet assembly") communicatively coupled to the console 110. For this embodiment, the stylet assembly 120 includes an elongate probe (e.g., stylet) 130 on its distal end 122 and a console connector 132 on its proximal end 124. The console connector 132 enables the stylet assembly 120 to be operably connected to the console 110 via an interconnect 140 including one or more optical fibers 142 (hereinafter, "optical fiber(s)") and a conductive medium 144 terminated by a single optical/electric connector 146 (or terminated by dual connectors. Herein, the connector 146 is configured to engage (mate) with the console connector 132 to allow for the propagation of light between the console 110 and the stylet assembly 120 as well as the propagation of electrical signals from the stylet 130 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The processor 160, with access to the memory 165 (e.g., non-volatile memory), is included to control functionality of the console 110 during operation. As shown, the display 165 may be a liquid crystal diode (LCD) display integrated into the console 110 and employed as a user interface to display information to the clinician, especially during a catheter placement procedure (e.g., cardiac catheterization). In another embodiment, the display 165 may be separate from the console 110. Although not shown, a user interface is configured to provide user control of the console 110.

For both of these embodiments, the content depicted by the display 165 may change according to which mode the stylet 130 is configured to operate: optical, TLS, ECG, or other modality. In TLS mode, the content rendered by the display 165 may constitute a two-dimensional (2-D) or three-dimensional (3-D) representation of the physical state (e.g., length, shape, form, and/or orientation) of the stylet 130 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below According to one embodiment of the disclosure, an activation control 126, included on the stylet assembly 120, may be used to set the stylet 130 into a desired operating mode and selectively alter operability the display 165 by the clinician to assist in medical device placement. For example, based on the modality of the stylet 130, the display 165 of the console 110 can be employed for optical modality-based guidance during catheter advancement through the vasculature or TLS modality to determine the physical state (e.g., length, form, shape, orientation, etc.) of the stylet 130. In one embodiment, information from multiple modes, such as optical, TLS or ECG for example, may be displayed concurrently (e.g., at least partially overlapping in time). In one embodiment, the display 165 is a liquid crystal diode (LCD) device.

Referring still to FIG. 1, the optical logic 180 is configured to support operability of the stylet assembly 120 and enable the return of information to the console 110, which may be used to determine the physical state associated with the stylet 130 along with monitored electrical signals such as ECG signaling via an electrical signaling logic 181 that supports receipt and processing of the received electrical signals from the stylet 130 (e.g., ports, analog-to-digital conversion logic, etc.). The physical state of the stylet 130 may be based on changes in characteristics of the reflected light signals 150 received from the stylet 130. The characteristics may include shifts in wavelength caused by strain on certain regions of the core fibers integrated within a multi-core optical fiber 135 positioned within or operating as the stylet 130, as shown below. From information associated with the reflected light signals 150, the console 110 may determine (through computation or extrapolation of the wavelength shifts) the physical state of the stylet 130, notably a catheter 195 configured to receive the stylet 130.

According to one embodiment of the disclosure, as shown in FIG. 1, the optical logic 180 may include a light source 182 and an optical receiver 184. The light source 182 is configured to transmit the broadband incident light 155 for propagation over the optical fiber(s) 142 included in the interconnect 140, which are optically connected to the multi-core optical fiber 135 within the stylet 130. In one embodiment, the light source 182 is a tunable swept laser, although other suitable light source can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 130 (see FIG. 2), and (ii) translate the reflected light signals 150 into reflection data 185, namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data 185 to the memory 165 for storage and processing by reflection data classification logic 190. The reflection data classification logic 190 may be configured to: (i) identify which core fibers pertain to which of the received reflection data 185 and (ii)

segregate the reflection data 185 provided from reflected light signals 150 pertaining to similar regions of the stylet 130 or spectral widths into analysis groups. The reflection data for each analysis group is made available to shape sensing analytic logic 192 for analytics.

According to one embodiment of the disclosure, the shape sensing analytic logic 192 is configured to compare wavelength shifts measured by sensors deployed in each periphery core fiber at the same measurement region of the stylet 130 (or same spectral width) to the wavelength shift at a center core fiber of the multi-core optical fiber 135 positioned along central axis and operating as a neutral axis of bending. From these analytics, the shape sensing analytic logic 192 may determine the shape the core fibers have taken in 3-D space and may further determine the current physical state of the catheter 195 in 3-D space for rendering on the display 170.

According to one embodiment of the disclosure, the shape sensing analytic logic 192 may generate a rendering of the current physical state of the stylet 130 (and potentially the catheter 195), based on heuristics or run-time analytics. For example, the shape sensing analytic logic 192 may be configured in accordance with machine-learning techniques to access a data store (library) with pre-stored data (e.g., images, etc.) pertaining to different regions of the stylet 130 (or catheter 195) in which reflected light from core fibers have previously experienced similar or identical wavelength shifts. From the pre-stored data, the current physical state of the stylet 130 (or catheter 195) may be rendered. Alternatively, as another example, the shape sensing analytic logic 192 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 130 (and/or catheter 195), especially to enable guidance of the stylet 130, when positioned at a distal tip of the catheter 195, within the vasculature of the patient and at a desired destination within the body.

The console 110 may further include electrical signal receiver logic 186, which is positioned to receive one or more electrical signals from the stylet 130. The stylet 130 is configured to support both optical connectivity as well as electrical connectivity. The electrical signal receiver logic 186 receives the electrical signals (e.g., ECG signals) from the stylet 130 via the conductive medium 144. The electrical signals may be processed by electrical signal analytic logic 194, executed by the processor 160, to determine ECG waveforms for display.

Figure 2:
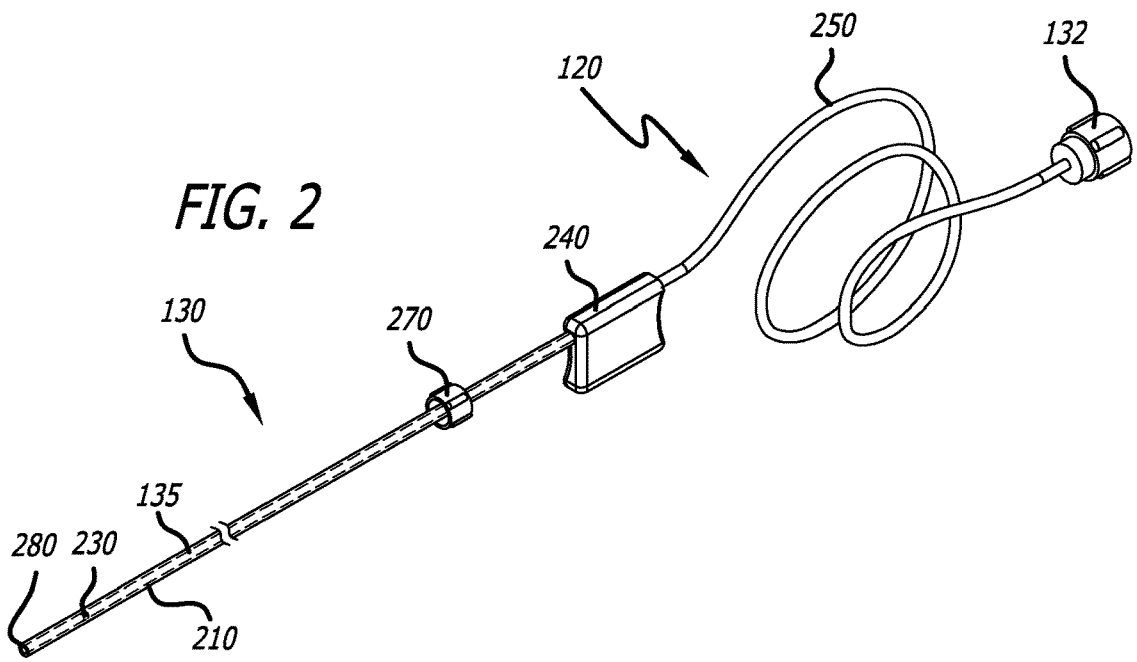
FIG. 2 is an exemplary embodiment of a stylet assembly of FIG. 1.

Referring now to FIG. 2, an exemplary embodiment of the stylet assembly 120 to be operably connected to the catheter 195 of FIG. 1 is shown. Herein, the stylet assembly 120 features the stylet 130, which includes an insulating layer 210 encasing a multi-core optical fiber 135 and/or conductive medium 230 as shown in FIGS. 6A-9B and described below. The stylet 130 extends distally from a handle 240 while an interconnect (e.g. tether) 250 extends proximally from the handle 240 and is terminated by the console connector 132 for coupling to the interconnect 140 of the console 110 as shown in FIG. 1. The handle 240 is included with the second interconnect (e.g., tether) 250 to assist with manipulation of the stylet 130 by the user during operation and may be configured to include activation controls 126 as shown in FIG. 1.

As shown, the stylet 130 and the interconnect 250 provide a pathway for outgoing optical signals produced by the light source 182 of the optical logic 180 and returning optical signals, produced by gratings within the core fibers of the multi-core optical fiber 135, for receipt by the photodetector 184 (see FIG. 1). Insulating layers associated with the stylet 130 and the interconnect 250 may vary in density and material to control its rigidity and mechanical properties.

Figure 3:
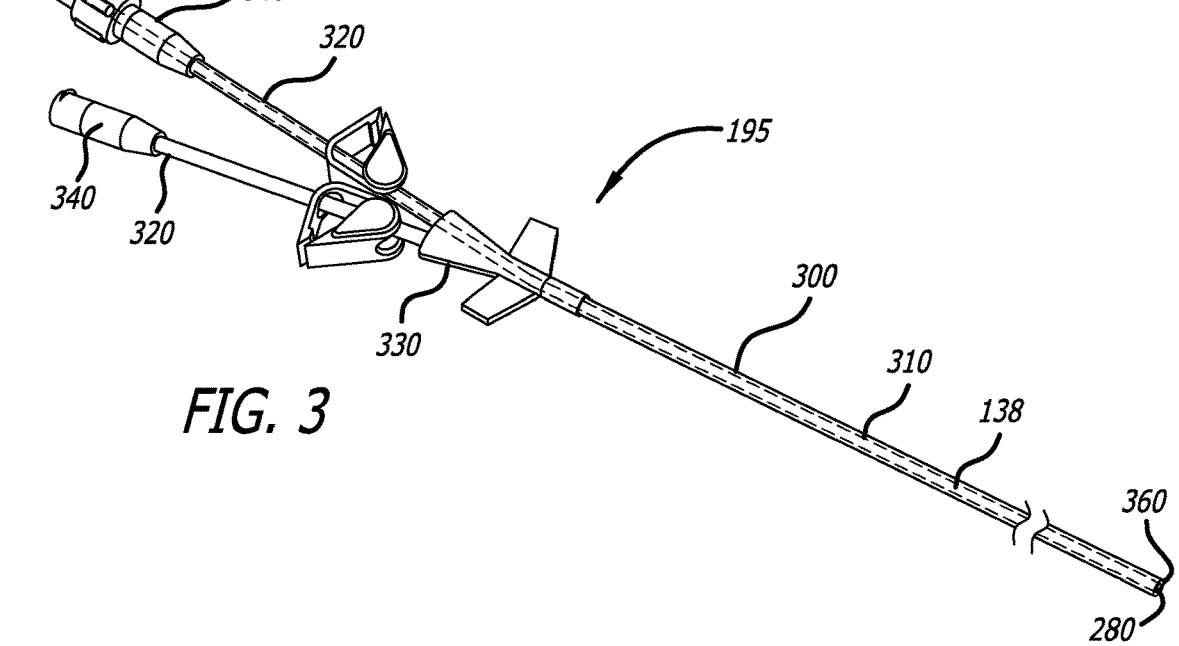
FIG. 3 is an embodiment of the stylet for placement within a catheter of FIG. 1.

Furthermore, according to one embodiment of the disclosure, the stylet assembly 120 further includes a catheter connector 270, which may be threaded for attachment to a connector of an extension leg of a catheter (see FIG. 3). This connectivity between the connector 270 and a connector of the extension leg connector may be used during the procedure of inserting the stylet 130 into a lumen of the catheter 195, as shown in FIG. 3. When deployed, a distal end of the multi-core optical fiber 135 need not be substantially co-terminal with a distal tip of the catheter. As will be seen, the returned optical signals (reflected light 150) from the sensors (reflective gratings) within each core fiber included with the multi-core optical fiber 135 may be analyzed during its advancement through the patient vasculature.

Note further that, it should appreciated that the term "stylet," as used herein, can include any one of a variety of devices configured for removable placement within a lumen of the catheter (or other portion of a medical device) to assist in placing a distal end of the catheter in a desired location within the patient's vasculature. Also, note that other connection schemes between the stylet 130 and the console 110 can also be used without limitation.

Referring to FIG. 3, an embodiment of the stylet 130 for placement within the catheter 195 is shown. Herein, the catheter 195 includes an elongate catheter tube 300 defining one or more lumens 310 extending between proximal and distal ends of the catheter tube 300. The catheter tube 300 is in communication with a corresponding extension leg 320 via a bifurcation hub 330. Luer connectors 340 are included on the proximal ends of the extension legs 320.

As shown, the stylet assembly 120 includes the console connector 132 on its proximal end 350 to enable the stylet 130 to operably connect with the console 110 (see FIG. 1). The interconnect 250 distally extends communications from the console 110 to the catheter connector 270, which is configured to threadably engage (or otherwise connect with) the Luer connector 340 of one of the extension legs 320 of the catheter 195. The stylet 130 extends distally from the catheter connector 270 up to a distal-end 280 of the stylet 130. The distal-end 280 of the stylet 130 may be substantially co-terminal with a distal tip 360 of the catheter 195 within the vasculature.

Figure 4:
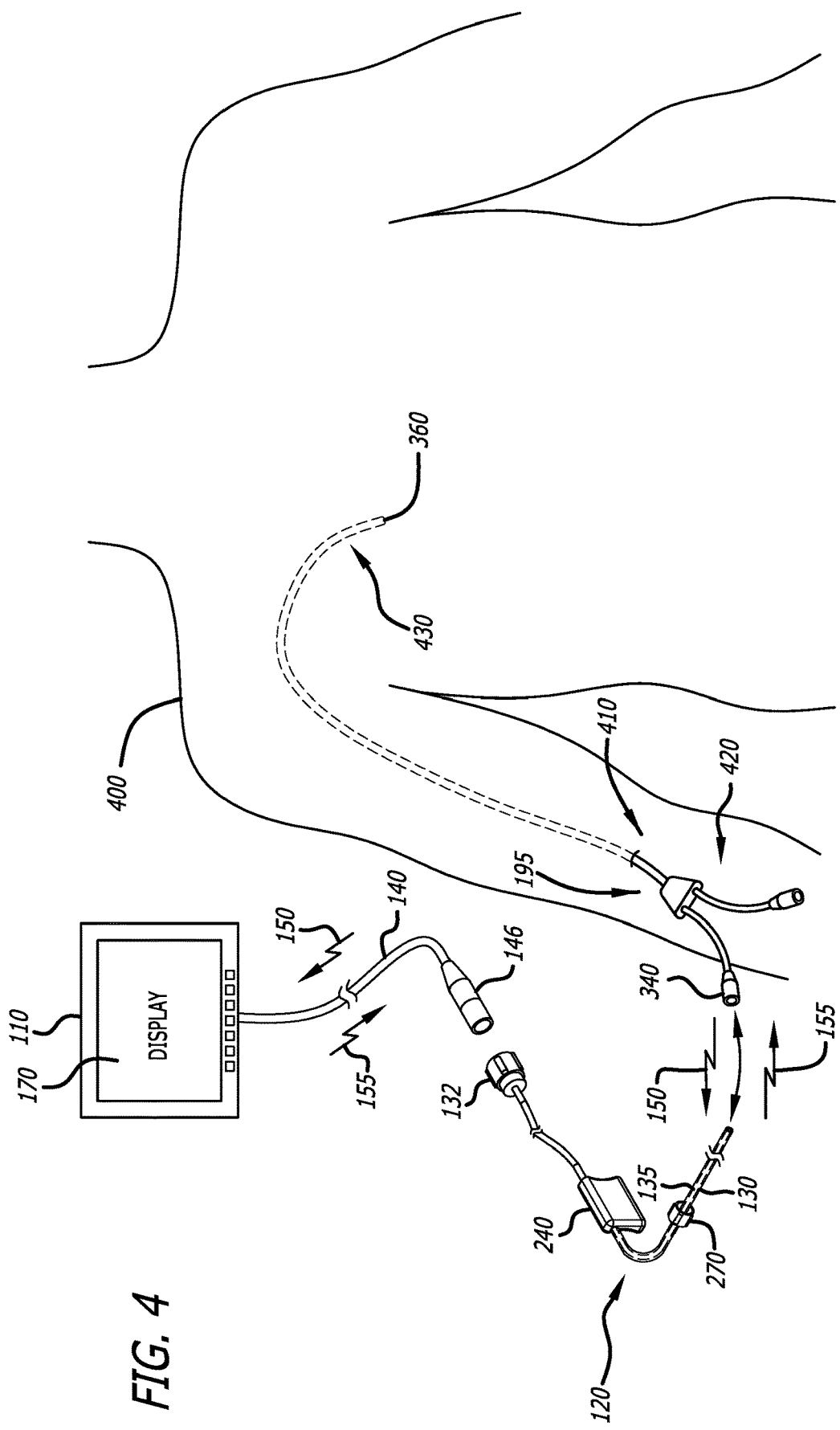
FIG. 4 is an embodiment of the stylet of FIGS. 1-3 inserted into a vasculature of a patient.

Referring now to FIG. 4, an embodiment of the stylet 130 illustrating its placement within the catheter 195 as the catheter 195 is being inserted into a vasculature of a patient 400 through a skin insertion site 410 is shown. As illustrated in FIG. 4, the catheter 195 generally includes a proximal portion 420 that generally remains exterior to the patient 400 and a distal portion 430 that generally resides within the patient vasculature after placement is complete. The stylet 130 is employed to assist in the positioning of the distal tip 360 of the catheter 195 in a desired position within the patient vasculature. In one embodiment, the desired position for the catheter distal tip 360 is proximate the patient's heart, such as in the lower one-third ($\frac{1}{3}^{rd}$) portion of the Superior Vena Cava ("SVC") for this embodiment. Of course, the stylet 130 can be employed to place the catheter distal tip 360 in other locations.

Figure 5:
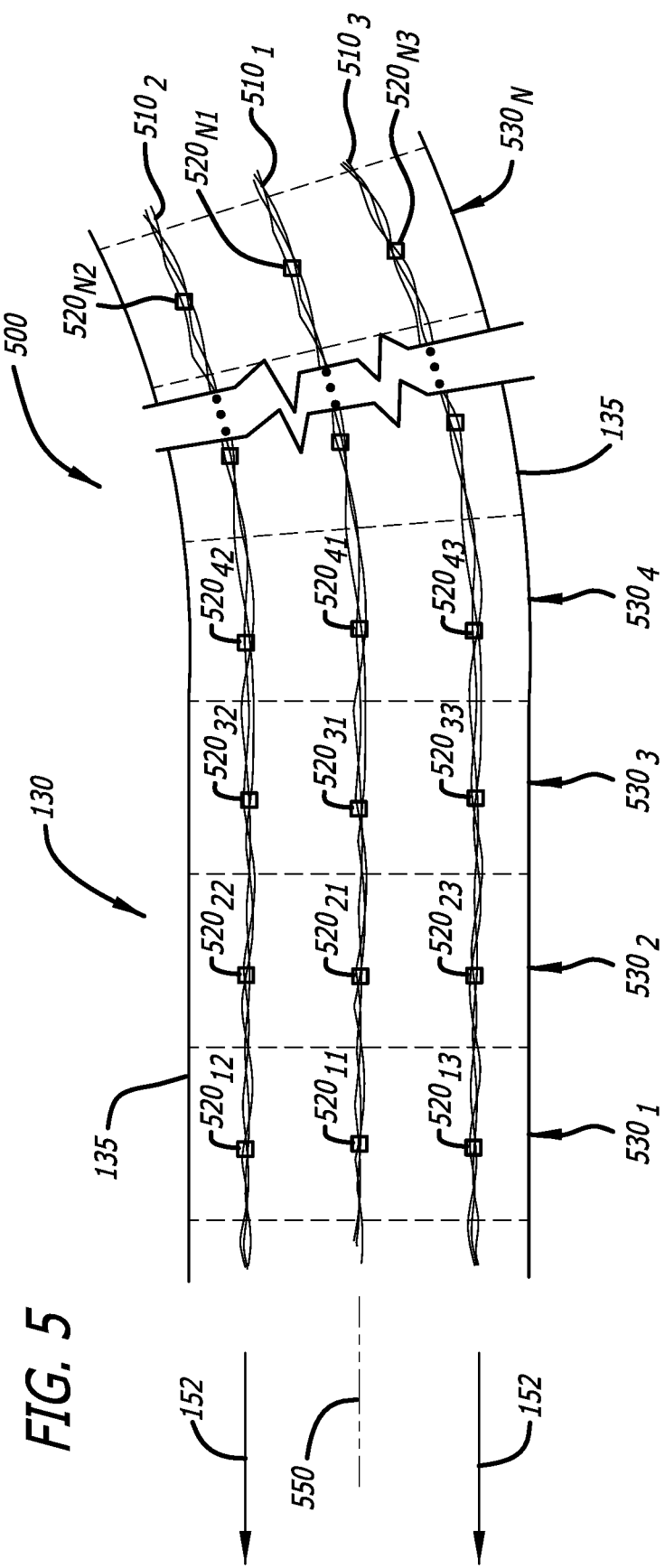
FIG. 5 is an exemplary embodiment of a structure of a section of the multi-core optical fiber included within the stylet 130 of FIGS. 1-3.

During advancement of the catheter 195, the stylet 130 receives broadband light 155 from the console 110 via interconnect 140, which includes the connector 146 for coupling to the console connector 132 for the stylet assembly 120. The reflected light 150 from sensors (reflective gratings) within each core fiber of the multi-core optical fiber 135 are returned from the stylet 130 over the interconnect 140 for processing by the console 120. The physical state of the stylet 130 may be ascertained based on analytics of the wavelength shifts of the reflected light 150. For example, the strain caused through bending of the stylet 130, and hence angular modification of each core fiber, causes different degrees of deformation. The different degrees of deformation alters the shape of the sensors (reflective grating) positioned on the core fiber, which may cause variations (shifts) in the wavelength of the reflected light from the sensors positioned on each core fiber within the multi-core optical fiber 135, as shown in FIG. 5. From this wavelength shifting, the shape sensing analytic logic 192 within the console 110 (see FIG. 1) may determine the physical state of the stylet 130 (e.g., shape, orientation, etc.).

Referring to FIG. 5, an exemplary embodiment of a right-sided, longitudinal view of a section 500 of the multi-core optical fiber 135 included within the stylet 130 is shown. The multi-core optical fiber section 500 depicts certain core fibers $510_1$-$510_M$ (M≥2, M=4 as shown) along with the spatial relationship between sensors (e.g., reflective gratings) $520_{11}$-$520_{NM}$ (N≥2; M≥2) present within the core fibers $510_1$-$510_M$, respectively. As shown, the section 500 is subdivided into a plurality of cross-sectional regions $530_1$-$530_N$, where each cross-sectional region $530_1$-$530_N$ corresponds to reflective gratings $520_{11}$-$520_{14}$ . . . $520_{N1}$-$520_{N4}$. Some or all of the cross-sectional regions $530_1$ . . . $530_N$ may be static (e.g., prescribed length) or may be dynamic (e.g., vary in size among the regions $530_1$ . . . $530_N$). A first core fiber $510_1$ is positioned substantially along a center (neutral) axis 550 while core fiber $510_2$ may be oriented within the cladding of the multi-core optical fiber 130, from a cross-sectional, front-facing perspective, to be position on "top" the first core fiber $510_1$. In this deployment, the core fibers $510_3$ and $510_4$ may be positioned "bottom left" and "bottom right" of the first core fiber $510_1$.

Referencing the first core fiber $510_1$ as an illustrative example, when the stylet 130 is operative, each of the reflective gratings $520_1$-520N reflect light for a different spectral width. As shown, each of the gratings $520_{1i}$-$520_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $510_2$-$510_3$ but along at the same cross-sectional regions $530$-$530_N$ of the multi-core optical fiber 135, the gratings $520_{12}$-$520_{N2}$ and $520_{13}$-$520_{N3}$ are configured to reflect incoming light at same (or substantially similar) center frequency. As a result, the reflected light returns information that allows for a determination of the physical state of the optical fiber 135 (and the stylet 130) based on wavelength shifts measured from the returned, reflected light. In particular, strain (e.g., compression or tension) applied to the multi-core optical fiber 135 (e.g., at least core fibers $510_2$-$510_3$) results in wavelength shifts associated with the returned, reflected light. Based on different locations, the core fibers $510_1$-$510_4$ experience different types and degree of strain based on angular path changes as the stylet 130 advances in the patient.

For example, with respect to the multi-core optical fiber section 500 of FIG. 5, in response to angular (e.g., radial) movement of the stylet 130 is in the left-veering direction, the fourth core fiber $510_4$ (see FIG. 6A) of the multi-core optical fiber 135 with the shortest radius during movement (e.g., core fiber closest to a direction of angular change) would exhibit compression (e.g., forces to shorten length). At the same time, the third core fiber $510_3$ with the longest radius during movement (e.g., core fiber furthest from the direction of angular change) would exhibit tension (e.g., forces to increase length). As these forces are different and unequal, the reflected light from reflective gratings $520_{N2}$ and $520_{N3}$ associated with the core fiber $510_2$ and $510_3$ will exhibit different changes in wavelength. The differences in wavelength shift of the reflected light signals 152 can be used to extrapolate the physical configuration of the stylet 130 by determining the degrees of wavelength change caused by compression/tension for each of the periphery fibers (e.g., the second core fiber $510_2$ and the third core fiber $510_3$) in comparison to the wavelength of the reference core fiber (e.g., first core fiber $510_1$) located along the neutral axis 550 of the multi-core optical fiber 135. These degrees of wavelength change may be used to extrapolate the physical state of the stylet 130.

Referring now to FIG. 6A, a first exemplary embodiment of the multimodal stylet 130 of FIG. 1 supporting both an optical and electrical signaling is shown. Herein, the stylet 130 features a centrally located multi-core optical fiber 135, which includes a cladding 600 and a plurality of core fibers $510_1$-$510_M$ (M≥2; M=4) residing within a corresponding plurality of lumens $620_1$-$620_M$. While the multi-core optical fiber 135 is illustrated within four (4) core fibers $510_1$-$510_4$, a greater number of core fibers $510_1$-$510_M$ (M≥4) may be deployed to provide a more detailed three-dimensional sensing of the physical state (e.g., shape, orientation, etc.) of the multi-core optical fiber 135 and the stylet 130 deploying the optical fiber 135, a greater number of core fibers $510_1$-$510_M$ (M≥4) may be deployed.

For this embodiment of the disclosure, the multi-core optical fiber 135 is encapsulated within a concentric braided tubing 610 positioned over a low-coefficient of friction layer 635. The braided tubing 610 may feature a "mesh" construction, in which the spacing between the intersecting conductive elements is selected based on the degree of rigidity desired for the stylet 130, as a greater spacing may provide a lesser rigidity, and thereby, a more pliable stylet 130.

According to this embodiment of the disclosure, as shown in FIGS. 6A-6B, the core fibers $510_1$-$510_4$ include (i) a central core fiber $510_1$ and (ii) a plurality of periphery core fibers $510_2$-$510_4$, which are maintained within lumens $620_1$-$620_4$ formed in the cladding 600. According to one embodiment of the disclosure, one or more of the lumen $620_1$-$620_4$ may be configured with a diameter sized to be greater than the diameter of the core fibers $510_1$-$510_4$. By avoiding a majority of the surface area of the core fibers $510_1$-$510_4$ from being in direct physical contact with a wall surface of the lumens $620_1$-$620_4$, the wavelength changes to the incident light are caused by angular deviations in the multi-core optical fiber 135 thereby reducing influence of compression and tension forces being applied to the walls of the lumens $620_1$-$620_M$, not the core fibers $510_1$-$510_M$ themselves.

As further shown in FIGS. 6A-6B, the core fibers $510_1$-$510_4$ may include central core fiber $510_1$ residing within a central or first lumen $620_1$ formed along the first neutral axis 550 and a plurality of core fibers $510_2$-$510_4$ residing within lumens $620_2$-$620_4$ each formed within different areas of the cladding 600 radiating from the first neutral axis 550. In general, the core fibers $510_2$-$510_4$, exclusive of the central core fiber $510_1$, may be positioned at different areas within a cross-sectional area 605 of the cladding 600 to provide sufficient separation to enable three-dimensional sensing of the multi-core optical fiber 135 based on changes in wavelength of incident light propagating through the core fibers $510_2$-$510_4$ and reflected back to the console for analysis.

For example, where the cladding 600 features a circular cross-sectional area 605 as shown in FIG. 6B, the core fibers $510_2$-$510_4$ may be positioned substantially equidistant from each other as measured along a perimeter of the cladding 600, such as at "top" (12 o'clock), "bottom-left" (8 o'clock) and "bottom-right" (4 o'clock) locations as shown. Hence, in general terms, the core fibers $510_2$-$510_4$ may be positioned within different segments of the cross-sectional area 605. Where the cross-sectional area 605 of the cladding 600 features a polygon cross-sectional shape (e.g., triangular, square, rectangular, pentagon, hexagon, octagon, etc.), the central core fiber $510_1$ may be located at or near a center of the polygon shape, while the remaining core fibers $510_2$-$510_M$ may be located proximate to angles between intersecting sides of the polygon shape.

Referring still to FIGS. 6A-6B, operating as the conductive medium for the stylet 130, the braided tubing 610 provides mechanical integrity to the multi-core optical fiber 135 and operates as a conductive pathway for electrical signals. For example, the braided tubing 610 may be exposed to a distal tip 630 of the stylet 130. The cladding 600 and the braided tubing 610, which is positioned concentrically surrounding a circumference of the cladding 600, are contained within the same insulating layer 650. The insulating layer 650 may be a sheath or conduit made of protective, insulating (e.g., non-conductive) material that encapsulates both for the cladding 600 and the braided tubing 610, as shown.

For one embodiment of the disclosure, a conductive material such as a conductive epoxy 640 may be affixed to the tip 630, where the braided tubing 610 and/or conductive epoxy 640 may be similarly joined with a termination/connection point created at the proximal portion of the stylet 130. It is contemplated that the handle 240 may include crimping/solder joints to assist in providing an electrical transition (electrical connection) between the braided tubing 610 within the stylet 130 and electrical wires in tether 250 that provides connectivity the interconnect 140 of the console 110. It is contemplated that other electrical connective mechanisms between the tether 250 and the braided tubing 610 may be deployed such as connectivity through abutment of the braided tubing 610 to a conductive element (mesh, gasket, or ring) located at proximal portion (or end) of the stylet 130 (with connectivity to tether 250), through abutment of the braided tubing 610 to conductive tabs/bars integrated into the handle 240 for routing through the tether 250, or through threaded action interface.

Referring now to FIG. 7A, a second exemplary embodiment of the multimodal stylet 130 of FIG. 1 supporting both an optical and electrical signaling is shown. Herein, the stylet 130 features the multi-core optical fiber 135 shown in FIG. 6A, which includes the cladding 600 and the first plurality of core fibers $510_1$-$510_M$ (M≥3; M=4 for embodiment) residing within the corresponding plurality of lumens $620_1$-$620_M$. For this embodiment of the disclosure, the multi-core optical fiber 135 includes the central core fiber $510_1$ residing within the central or first lumen $620_1$ formed along the first neutral axis 550 and the second plurality of core fibers $510_2$-$510_4$ residing within corresponding lumens $620_2$-$620_4$ positioned in different segments within the cross-sectional area 605 of the cladding 600. Herein, the core fibers $510_1$-$510_M$ may be deployed in a manner similar to the deployment described above and illustrated in FIGS. 6A-6B.

In contrast of the use of the braided tubing 610 illustrated in FIGS. 6A-6B, the multi-core optical fiber 135 of the multimodal stylet 130 may be paired with a conductive medium 700 such as an electrical wire. According to this embodiment of the disclosure, as shown in FIG. 7A, the conductive medium 700 is configured to propagate electrical (e.g., ECG) signals received by the stylet 130 upon placement of the stylet 130 within a patient. For this embodiment, the conductive medium 700 is positioned without being isolated from the multi-core optical fiber 135, where the conductive medium 700 extends lengthwise adjacent to an outer surface 710 of the cladding 600.

For one embodiment of the disclosure, the handle 240 may include crimping/solder joints to provide electrical connectivity between the conductive medium 700 within electrical wires within the tether 250. It is contemplated that other electrical connective mechanisms to the conductive medium may be deployed as described above.

As illustrated by a cross-sectional view of the stylet 130 in FIGS. 7B-7C, the multi-core optical fiber 135 and the conductive medium 700 may be positioned in parallel, where the optical fiber 135 and the conductive medium 700 are encapsulated within the same insulating layer 720. For this embodiment of the disclosure, the insulating layer 720 operates as a protective casing for both the multi-core optical fiber 135 and the conductive medium 700, where the conductive medium 700 may be in direct physical contact with the cladding 600. As shown in FIG. 7B, the insulating layer 720 operates as a single casing in which the conductive medium 700 is not shielded (insulated) from the cladding 600 of the multi-core optical fiber 135. In contrast, as shown in FIG. 7C, the insulating layer 720 operates as a dual casing in which the conductive medium 700 is shielded (insulated) from the cladding 600 of the multi-core optical fiber 135.

Referring to FIG. 8A, a third exemplary embodiment of the multimodal stylet 130 of FIG. 1 supporting both an optical and electrical signaling is shown. Herein, the multimodal stylet 130 features the multi-core optical fiber 135 shown in FIG. 6A, which includes the cladding 600 and the first plurality of core fibers $510_1$-$510_M$ (M≥3; M=4 for embodiment) residing within the corresponding plurality of lumens $620_1$-$620_M$. For this embodiment of the disclosure, the multi-core optical fiber 135 includes the central core fiber $510_1$ residing within the central or first lumen $620_1$ formed along the first neutral axis 550 and the second plurality of core fibers $510_2$-$510_4$ residing within corresponding lumens $620_2$-$620_4$ positioned in different segments within the cross-sectional area 605 of the cladding 600. Herein, the multi-core optical fiber 135 may be paired with a flex circuit 800, namely a flexible printed circuit running along a length of the multi-core optical fiber 135.

As shown in FIGS. 8A-8B, the flex circuit 800 is configured to propagate any electrical (e.g., ECG) signals detected by the stylet 130. The flex circuit 800 resides along an outer surface 810 of the cladding 600 and may be encased within an insulating layer (conduit) 820. According to one embodiment of the disclosure, the flex circuit 800 may be attached to the cladding 600 of the multi-core optical fiber 135 through one or more electrical attachment members 820, which may be electrically isolated from the multi-core optical fiber 135. The electrical attachment members 820 may feature a crimping mechanism, one or more solder joints, or the like. For example, the handle 240 of the stylet assembly 120 of FIG. 1, which is attached to the stylet 130, may act as the crimping mechanism to establish connectivity between the flex circuit and electrical wires provided via the tether 250 of the stylet assembly 120.

Referring now to FIG. 9A, a fourth exemplary embodiment of the multimodal stylet 130 of FIG. 1 supporting both an optical and electrical signaling is shown. Herein, the multimodal stylet 130 features the multi-core optical fiber 135 described above and shown in FIG. 6A, which includes the cladding 600 and the first plurality of core fibers $510_1$-$510_M$ (M≥3; M=4 for embodiment) residing within the corresponding plurality of lumens $620_1$-$620_M$. For this embodiment of the disclosure, the multi-core optical fiber 135 includes the central core fiber $510_1$ residing within the central or first lumen $620_1$ formed along the first neutral axis 550 and the second plurality of core fibers $510_2$-$510_4$ residing within corresponding lumens $620_2$-$620_4$ positioned in different segments within the cross-sectional area 605 of the cladding 600. Herein, the multi-core optical fiber 135 is encapsulated within a conductive tubing 900. The conductive tubing 900 may feature a "hollow" conductive cylindrical member concentrically encapsulating the multi-core optical fiber 135. Such conductive tubing 900 can be formed of a metal or ally including a shape-memory alloy such as nitinol.

Referring to FIGS. 9A-9B, operating as a conductive medium for the stylet 130 in the transfer of electrical signals (e.g., ECG signals) to the console, the conductive tubing 900 may be exposed up to a tip 910 of the stylet 130. For this embodiment of the disclosure, a conductive epoxy 920 (e.g., metal-based epoxy such as a silver epoxy) may be affixed to the tip 910 and similarly joined with a termination/connection point created at a proximal end 930 of the stylet 130. The electrical pathway may be continued through the handle 240 to the connector 132 located on the proximal end 124 of the interconnect 144 of the stylet assembly 120 as shown in FIG. 1. Alternatively, the handle 240 may provide an electrical coupling between the conductive tubing 900 and an electrical wire included as part of the interconnect 144 with the multi-core optical fiber 330. The cladding 600 and the conductive tubing 900, which is positioned concentrically surrounding a circumference of the cladding 600, are contained within the same insulating layer 940. The insulating layer 940 may be a protective conduit encapsulating both for the cladding 600 and the conductive tubing 900, as shown.

Referring now to FIG. 10A, a fifth exemplary embodiment of the multimodal stylet 130 of FIG. 1 supporting both an optical and electrical signaling is shown. Herein, the stylet 130 features the multi-core optical fiber 135 shown in FIG. 6A, which includes the cladding 600 and the first plurality of core fibers $510_1$-$510_M$ (M≥3; M=4 for embodiment) residing within the corresponding plurality of lumens $620_1$-$620_M$. For this embodiment of the disclosure, the multi-core optical fiber 135 includes the central core fiber $510_1$ residing within the central or first lumen $620_1$ formed along the first neutral (e.g., central) axis 550 and the second plurality of core fibers $510_2$-$510_4$ residing within corresponding lumens $620_2$-$620_4$ positioned in different segments within the cross-sectional area 605 of the cladding 600. Herein, the core fibers $510_1$-$510_M$ may be deployed in a manner similar to the deployment described above and illustrated in FIGS. 7A-7C.

In contrast of the paired optical-wire deployment of FIG. 7A, the conductive medium 1000 is contained with a channel 1010 into which a portion of the multi-core optical fiber 135 resides, where the conductive medium 1000 may extend lengthwise and remain adjacent to a segment 1020 of the surface area of the cladding 600. The degree of containment may include the multi-core optical fiber 135 being at least partially encapsulated (see FIG. 10C) or substantially encapsulated (see FIG. 10D) within the channel 1010 of the conductive medium 1000. As shown in FIG. 10C, a portion of the circumference of the multi-core optical fiber 135 (e.g., ranging between forty to sixty percent of the circumference) may be retained within the channel 1010, where a first channel edge 1030 to a second channel edge 1040 may extend slightly beyond a diametrical bisection of the cross-sectional area 605 of the conductive medium 1000. In FIG. 10D, a greater portion of the circumference of the multi-core optical fiber 135 (e.g., greater than sixty percent of the circumference) may be retained within the channel 1010, causing the optical fiber 135 to be "snapped" into the channel 1000 as an opening 1060 of the channel 1010 may be smaller in width than the width of the channel 1065 in which the optical fiber 135 is retained as well as an opening 1070 of the channel 1010 as illustrated in FIG. 10C (but just larger, equal or just smaller than the width of the sheath of the optical fiber as the sheath is made of a flexible material).

As illustrated by a cross-sectional view of a first embodiment of the stylet 130, in FIG. 10B, the multi-core optical fiber 135 and the conductive medium 1000 may be positioned in parallel, where the optical fiber 135 resides within the channel 1010, formed as a recess or grooved portion on the conductive medium (e.g., wire) 1000, and encapsulated within optional insulating layer 1050. For this embodiment of the disclosure, the insulating layer 1050 operates as a protective casing for both the multi-core optical fiber 135 and the conductive medium 1000, where the conductive medium 1000 may be in direct physical contact with the cladding 600 as shown or may be insulated (shielded) from the cladding 600. Cross-sectional views of other embodiments of the stylet 130, with greater encapsulation of the optical fiber 135 within the channel 1010, are shown in FIGS. 10C-10D.

Figure 11B:
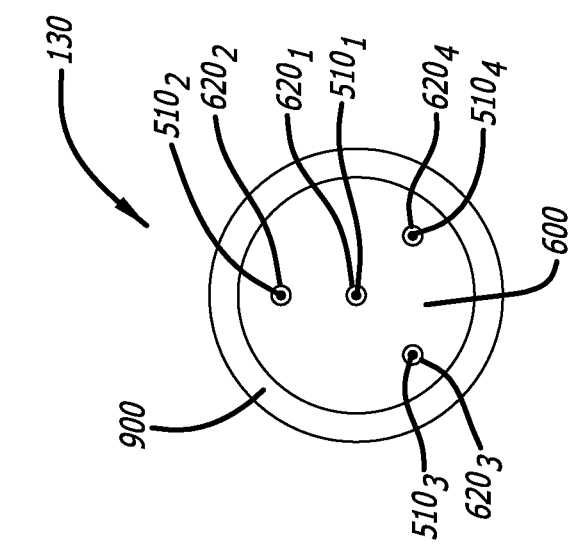
FIG. 11B is a cross sectional view of the multimodal stylet of FIG. 11A.
Figure 11A:
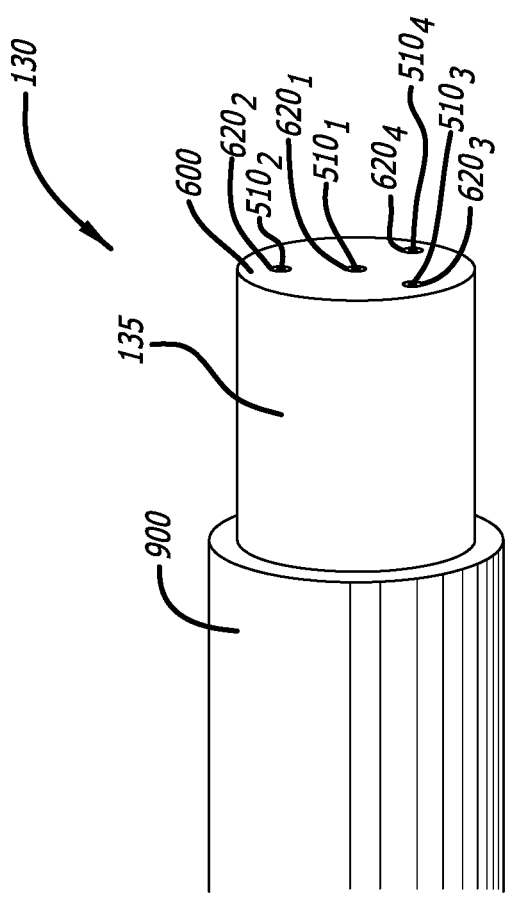
FIG. 11A is a sixth exemplary embodiment of the multimodal stylet of FIG. 1.

Referring now to FIGS. 11A and 111B, a sixth exemplary embodiment of the multimodal stylet 130 of FIG. 1 supporting both an optical and electrical signaling is shown. Herein, the stylet 130 features the multi-core optical fiber 135 shown in FIG. 6A, which includes the cladding 600 and the first plurality of core fibers $510_1$-$510_M$ (M≥3; M=4 for embodiment) residing within the corresponding plurality of lumens $620_1$-$620_M$ as set forth above in the description of the fourth exemplary embodiment of the multimodal stylet 130 of FIGS. 9A and 9B, which description is incorporated herein so as to not burden the disclosure. However, different than the multimodal stylet 130 of FIGS. 9A and 9B, the multi-core optical fiber 135 is encapsulated within only the conductive tubing 900 and optionally affixed thereto with the conductive epoxy 920; the insulating layer 940 shown in FIGS. 9A and 9B is not included. The conductive tubing 900 may feature a "hollow" conductive cylindrical member concentrically encapsulating the multi-core optical fiber 135. Such conductive tubing 900 can be formed of a metal or ally including a shape-memory alloy such as nitinol.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical device, comprising:
a multi-core optical fiber including a cladding and one or more core fibers spatially arranged within the cladding, each core fiber of the one or more core fibers including a plurality of sensors distributed along a longitudinal length thereof and each sensor of the plurality of sensors being configured to:
(i) reflect a light signal as reflected light with a different spectral width based on received incident light, and
(ii) change a characteristic of the reflected light for use in determining a physical state of the multi-core optical fiber;
a conductive medium configured to provide a pathway for electrical signals detected at a distal portion of the conductive medium; and
an insulating layer, wherein the multi-core optical fiber is encapsulated in the insulating layer and the conductive medium is encapsulated within the insulating layer.

2. A medical device, comprising:
a multi-core optical fiber including a cladding and one or more core fibers spatially arranged within the cladding, each core fiber of the one or more core fibers including a plurality of sensors distributed along a longitudinal length of each core fiber and each sensor of the plurality of sensors being configured to:
(i) reflect a light signal as reflected light with a different spectral width based on received incident light, and
(ii) change a characteristic of the reflected light for use in determining a physical state of the multi-core optical fiber; and
a conductive medium configured to provide a pathway for electrical signals detected at a distal portion of the conductive medium, wherein the conductive medium includes one or more channels along a surface of the conductive medium, and wherein each channel of the one or more channels is configured to retain at least one core fiber of the one or more core fibers.

3. The medical device as defined in claim 1, wherein the medical device corresponds to a multimodal stylet.

4. The medical device as defined in claim 1, wherein each sensor of the plurality of sensors constitutes a reflective grating positioned at a different region along the longitudinal length of each core fiber.

5. The medical device as defined in claim 1, wherein the change in the characteristic of the reflected light includes a shift in wavelength applied to the reflected light to identify at least a type of strain.

6. The medical device as defined in claim 5, wherein the type of strain is a compression or a tension.

7. The medical device as defined in claim 1, wherein the electrical signals include an electrocardiogram (ECG) signal.

8. The medical device as defined in claim 1, wherein the conductive medium corresponds to a braided tubing positioned concentric to the cladding of the multi-core optical fiber.

9. The medical device as defined in claim 8, wherein a distal end of the braided tubing and distal ends of each core fiber of the one or more core fibers are exposed at a distal end of the medical device.

10. The medical device as defined in claim 9, further comprising:
a conductive material positioned at least at the distal end of the braided tubing and positioned to electrically couple the distal end of the braided tubing to an electrical termination point positioned at a proximal end of the medical device.

11. The medical device as defined in claim 1, wherein the conductive medium corresponds to a conductive tubing positioned concentric to the cladding of the multi-core optical fiber.

12. The medical device as defined in claim 11, wherein the conductive tubing is nitinol tubing.

13. The medical device as defined in claim 11, wherein the conductive tubing is not encapsulated in the insulating layer.

14. The medical device as defined in claim 1, wherein the conductive medium includes one or more electrical wires positioned within a first insulating-layer lumen formed by the insulating layer while the cladding of the multi-core optical fiber is positioned within a second insulating-layer lumen formed by the insulating layer.

15. The medical device as defined in claim 14, wherein the one or more electrical wires and the multi-core optical fiber are electrically isolated by a portion of the first insulating-layer lumen, a portion of the second insulating-layer lumen, or portions of the first insulating-layer lumen and the second insulating-layer lumen.

16. The medical device as defined in claim 1, wherein the conductive medium includes a flexible circuit residing along an outer surface of the cladding and distributed along a length of the multi-core optical fiber.

17. The medical device as defined in claim 1, wherein the one or more core fibers comprise a central core fiber residing within a central cladding lumen formed along a first axis and two or more core fibers each residing within two or more respective cladding lumens formed within a different area of the cladding parallel to the first axis.

18. The medical device as defined in claim 17, wherein the first axis is a central axis for the multi-core optical fiber having a circular cross-sectional area with the two or more core fibers including:
a first core fiber residing within a first cladding lumen positioned within a first arc segment of the circular cross-sectional area in a first radial direction from the central cladding lumen,
a second core fiber residing within a second cladding lumen positioned within a second arc segment of the circular cross-sectional area separate from the first arc segment in a second radial direction from the first cladding lumen, and
a third core fiber residing within a third cladding lumen positioned within a third arc segment of the circular cross-sectional area separate from both the first arc segment and the second arc segment in a third radial direction from the first cladding lumen.

19. The medical device as defined in claim 1, wherein the one or more core fibers comprise a central core fiber residing within a central cladding lumen formed along a central axis of the cladding and each core fiber of two or more core fibers residing within a lumen parallel to the central axis such that each core fiber is radially positioned closer to an edge of the cladding than the central core fiber.

20. The medical device as defined in claim 19, wherein the two or more core fibers include a first core fiber residing within a first cladding lumen formed coplanar to the central cladding lumen, a second core fiber residing within a second cladding lumen positioned radially from the central cladding lumen forming a first obtuse angle between the first cladding lumen and the second cladding lumen, and a third core fiber residing within a third cladding lumen positioned radially from the central cladding lumen forming a second obtuse angle between the first cladding lumen and the third cladding lumen and a third obtuse angle between the second cladding lumen and the third cladding lumen.

21. The medical device as defined in claim 1, wherein the physical state of the multi-core optical fiber includes one or more of a length, a shape, a form, or an orientation as instantly possessed by the multi-core optical fiber or a portion of the multi-core optical fiber.

22. The medical device as defined in claim 21, wherein the physical state of the multi-core optical fiber being implemented within a stylet represents an instant physical state of a catheter into which the stylet is inserted during advancement of the catheter into a body of a patient.

23. The medical device as defined in claim 1, wherein the multi-core optical fiber is positioned to reside within a channel of the conductive medium.

24. The medical device as defined in claim 23, wherein the conductive medium is an electrical wire including a groove along a surface of the electrical wire to form the channel.

25. The medical device as defined in claim 1, wherein the conductive medium includes one or more channels along a surface of the conductive medium, and wherein each channel of the one or more channels is configured to retain at least one core fiber of the one or more core fibers.

26. A medical device, comprising:
   a multi-core optical fiber including a cladding and one or more core fibers spatially arranged within the cladding, each core fiber of the one or more core fibers including a plurality of sensors distributed along a longitudinal length of each core fiber and each sensor of the plurality of sensors being configured to:
   (i) reflect a light signal as reflected light with a different spectral width based on received incident light, and
   (ii) change a characteristic of the reflected light for use in determining a physical state of the multi-core optical fiber; and
   a conductive medium configured to provide a pathway for electrical signals detected at a distal portion of the conductive medium, the conductive medium comprising a braided tubing positioned concentric to the cladding of the multi-core optical fiber, wherein a distal end of the braided tubing and a distal end of each core fiber of the one or more core fibers are exposed at a distal end of the medical device.

27. The medical device as defined in claim 26, further comprising a conductive material positioned at least at the distal end of the braided tubing and positioned to electrically couple the distal end of the braided tubing to an electrical termination point positioned at a proximal end of the medical device.

28. A medical device, comprising:
   a multi-core optical fiber including a cladding and one or more core fibers spatially arranged within the cladding, the one or more core fibers comprising a central core fiber residing within a central cladding lumen formed along a first axis and two or more core fibers each residing within two or more respective cladding lumens formed within a different area of the cladding parallel to the first axis, each core fiber of the one or more core fibers including a plurality of sensors distributed along a longitudinal length of each core fiber and each sensor of the plurality of sensors being configured to:
   (i) reflect a light signal as reflected light with a different spectral width based on received incident light, and
   (ii) change a characteristic of the reflected light for use in determining a physical state of the multi-core optical fiber; and
   a conductive medium configured to provide a pathway for electrical signals detected at a distal portion of the conductive medium.

29. The medical device as defined in claim 28, wherein the first axis is a central axis for the multi-core optical fiber having a circular cross-sectional area with the two or more core fibers including:
   a first core fiber residing within a first cladding lumen positioned within a first arc segment of the circular cross-sectional area in a first radial direction from the central cladding lumen,
   a second core fiber residing within a second cladding lumen positioned within a second arc segment of the circular cross-sectional area separate from the first arc segment in a second radial direction from the first cladding lumen, and
   a third core fiber residing within a third cladding lumen positioned within a third arc segment of the circular cross-sectional area separate from both the first arc segment and the second arc segment in a third radial direction from the first cladding lumen.

30. A medical device, comprising:
   a multi-core optical fiber including a cladding and one or more core fibers spatially arranged within the cladding, the one or more core fibers comprising a central core fiber residing within a central cladding lumen formed along a central axis of the cladding and each core fiber of two or more core fibers residing within a lumen parallel to the central axis such that each core fiber is radially positioned closer to an edge of the cladding than the central core fiber, each core fiber of the one or more core fibers including a plurality of sensors distributed along a longitudinal length of each core fiber and each sensor of the plurality of sensors being configured to:
   (i) reflect a light signal as reflected light with a different spectral width based on received incident light, and
   (ii) change a characteristic of the reflected light for use in determining a physical state of the multi-core optical fiber; and
   a conductive medium configured to provide a pathway for electrical signals detected at a distal portion of the conductive medium.

31. The medical device as defined in claim 30, wherein the two or more core fibers include a first core fiber residing within a first cladding lumen formed coplanar to the central cladding lumen, a second core fiber residing within a second cladding lumen positioned radially from the central cladding lumen forming a first obtuse angle between the first cladding lumen and the second cladding lumen, and a third core fiber residing within a third cladding lumen positioned radially from the central cladding lumen forming a second obtuse angle between the first cladding lumen and the third cladding lumen and a third obtuse angle between the second cladding lumen and the third cladding lumen.

32. A medical device, comprising:
   a multi-core optical fiber including a cladding and one or more core fibers spatially arranged within the cladding, each core fiber of the one or more core fibers including a plurality of sensors distributed along a longitudinal length thereof and each sensor of the plurality of sensors being configured to:
   (i) reflect a light signal as reflected light with a different spectral width based on received incident light, and (ii) change a characteristic of the reflected light for use in determining a physical state of the multi-core optical fiber; and a conductive medium configured to provide a pathway for electrical signals detected at a distal portion of the conductive medium, wherein the multi-core optical fiber is positioned to reside within a channel of the conductive medium.

33. The medical device as defined in claim 32, wherein the conductive medium is an electrical wire including a groove along a surface of the electrical wire to form the channel.

\* \* \* \* \*